United States Patent [19]
Saiki et al.

[11] Patent Number: 5,336,772
[45] Date of Patent: Aug. 9, 1994

[54] METHOD FOR PREPARING N-FLUOROPYRIDINIUM SALT

[75] Inventors: Yukinori Saiki; Kazunori Nukui, both of Tokyo, Japan

[73] Assignee: Onoda Cement Co., Ltd., Onoda, Japan

[21] Appl. No.: 813,477

[22] Filed: Dec. 26, 1991

[30] Foreign Application Priority Data

Jan. 11, 1991 [JP] Japan .................. 3-012583

[51] Int. Cl.$^5$ .................... C07D 213/00
[52] U.S. Cl. .................... 546/286; 546/287; 546/288; 546/289; 546/290; 546/294; 546/295; 546/296; 546/297; 546/298; 546/300; 546/309; 546/340; 546/345
[58] Field of Search ............ 546/345, 290, 294, 295, 546/296, 297, 298, 300, 309, 286, 287, 288, 289, 340

[56] References Cited

U.S. PATENT DOCUMENTS 4,996,320 2/1991 Umemoto et al. .................. 546/345
5,081,249 1/1992 Umemoto ........................... 546/345

FOREIGN PATENT DOCUMENTS 0204535 12/1986 European Pat. Off. ............ 546/345
2231474 9/1990 Japan .

*Primary Examiner*—C. Warren Ivy
*Assistant Examiner*—A. A. Owens
*Attorney, Agent, or Firm*—Olson & Hierl, Ltd.

[57] ABSTRACT

N-fluoropyridinium salts of the following formula are prepared by reacting a pyridine compound with a Brønsted acid and fluorine, wherein the reaction solvent contains a greater than equimolar amount of the pyridine compound relative to an amount of the Brønsted acid.

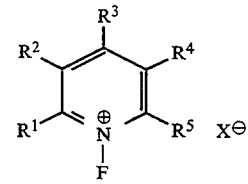

The method can produce N-fluoropyridinium salts with a high yield.

18 Claims, No Drawings

METHOD FOR PREPARING N-FLUOROPYRIDINIUM SALT

BACKGROUND OF THE INVENTION

1. Field of the Invention

The present invention relates to a method for preparing N-fluoropyridinium salt. More particularly, the present invention relates to a method for preparing N-fluoropyridinium salt with a high yield.

2. Description of the Related Art

In reactions with organic compounds, fluorine, contrary to chlorine, bromine and iodine, reacts very violently, readily giving rise to the fission of the C—C bond of organic compounds and in cases where the reaction is excessively violent, fire or explosion in turn can break out.

For the purpose resolving the above problem, a fluorinating agent which can introduce fluorine to organic compounds under mild conditions has been developed. The present applicant has earlier found that N-fluoropyridinium salt obtained by reacting pyridine compounds with Brønsted acids or Lewis acids is an excellent fluorinating agent which satisfied these requirements (Japanese Patent Publication No.2-33707). Having high reactivity and selectivity to a variety of organic compounds, the N-fluoropyridinium salt is very useful for preparing fluorocompounds.

However, there is a problem in that the above mentioned Japanese Parent's method for preparing N-fluoropyridinium salt only produces the desired compound with a low yield. Therefore, a more improved method for preparing the same on an industrial scale is required.

As a result of intensive research to overcome this problem, the present inventors have found surprisingly that the use of an amount of a pyridine compound greater than an equimolar amount of a Brønsted acid improves the yield remarkably to achieve the present invention.

SUMMARY OF THE INVENTION

Accordingly, an object of the present invention is to provide a method for preparing N-fluoropyridinium salt of the general formula (I):

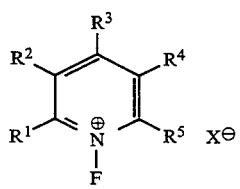

by reacting a pyridine compound of the following formula (II) with a Brønsted acid of the general formula XH and fluorine characterized by using an amount of pyridine compound greater than an equimolar amount of Brønsted acid:

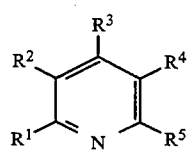

wherein $R^1$ to $R^5$ represent a hydrogen atom, a halogen atom, an alkyl, aryl, acyl, alkoxycarbonyl, aryloxycarbonyl, carbamoyl, nitro, cyano, alkylsulfonyl, arylsulfonyl, hydroxy, alkoxy, aryloxy, acyloxy, acylthio, amido, alkanesulfonyloxy or arenesulfonyloxy group; $X^\ominus$ represents a conjugate base of a Brønsted acid except for $F^\ominus$, $Cl^\ominus$, $Br^\ominus$ and $I^\ominus$ which are conjugate bases of hydrogen halides; $R^1$ $R^2$ $R^3$ $R^4$ and $R^5$ may combine directly or through a hereto-atom or atoms to form a cyclic structure, while $X^\ominus$ may be combined directly or through a hereto-atom or atoms with $R^1$ $R^2 R^3$, $R^4$ and $R^5$ in various combinations; and H is hydrogen.

DETAILED DESCRIPTION OF THE PREFERRED EMBODIMENTS

The present invention is further illustrated by the following.

Pyridine Compounds

Examples of pyridine compounds of general formula (II) used in the method of the present invention include: straight, branched or cyclic alkylated pyridine such as pyridine, (trifluoromethyl)pyridine, bis(trifluoromethyl)pyridine, tris(trifluoromethyl)pyridine, (trichloromethyl)pyridine, (pentafluoroethyl)pyridine, (pentafluorooctyl)pyridine, (methoxymethyl)pyridine, ethyl pyridylacetate, pyridylacetonitrile, pyridylacetone and the like; halopyridine such as chloropyridine, bromopyridine, fluoropyridine, dichloropyridine, difluoropyridine, trichloropyridine, tetrachloropyridine, pentachloropyridine, difluoropyridine, trifluoropyridine, pentafluoropyridine, chlorofluoropyridine, dichlorofluoropyridine and the like; (alkoxycarbonyl) or (aryloxycarbonyl)pyridine such as (trifluoromethyl)chloropyridine, (trifluoromethyl)dichloropyridine, (trifluoromethyl)trichloropyridine, (trifluoromethyl)fluoropyridine, methylchloropyridine, phenylpyridine, diphenylpyridine, triphenylpyridine, dipyridyl, acetylpyridine, bisacetylpyridine, (methoxycarbonyl)pyridine, (ethoxycarbonyl)pyridine, (butoxycarbonyl)pyridine, bis(ethoxycarbonyl)pyridine, bis(trifluoroethoxycarbonyl)pyridine, tris(methoxycarbonyl)pyridine, (phenoxycarbonyl)pyridine and the like; and 2,3-pyridinedicarboxylic anhydride, nitropyridine, cyanopyridine, dicyanopyridine, tricyanopyridine, benzenesulfonylpyridine, methylsulfonylpyridine, chlorocyanopyridine, folmylpyridine, (haloformyl) pyridine, nicotinamide, picolinamide, (dimethylaminocarbonyl) pyridine, methoxypyridine, dimethoxypyridine, propoxypyridine, butoxypyridine, menthoxypyridine, trifluoromethoxypyridine, acetoxypyridine, trifluoroacetoxypyridine, phenoxypyridine, acetylthiopyridine, methanesulfonyloxypyridine, benzenesulfonyloxypyridine, acetylaminopyridine, 2,3-tetramethylenepyridine, 3-hydroxypyridine, 1,2,3,4,5,6,7,8,-octahydroacridine and the like. (Brønsted acids)

Examples of Brønsted acids having a general formula XH include: sulfonic acids such as methanesulfonic acid, butanesulfonic acid, benzenesulfonic acid, toluenesulfonic acid, nitrobenzenesulfonic acid, dinitrobenzenesulfonic acid, trinitrobenzenesulfonic acid, trifluoromethanesulfonic acid, perfluorobutanesulfonic acid, perfluorooctanesulfonic acid, trichloromethanesulfonic acid, difluoromethanesulfonic acid, trifluoroethanesulfonic acid, fluorosulfonic acid, chlorosulfonic acid, monomethylsulfuric acid, sulfuric acid, camphorsulfonic acid, bromocamphorsulfonic acid, $\Delta^4$-cholestene-3-on-6sulfonic acid, 1-hydoxy-p-methane-2-sulfonic acid, p-styrenesulfonic acid, β-styrenesulfonic acid, poly(pstyrenesulfonic acid), vinylsulfonic acid, poly(vinylsulfonic acid), poly(2-acrylamide-2-methyl-1-propanesulfonic acid) and a copolymer of said propanesulfonic acid with styrene, perfluoro-3,6-dioxa-4-methyl-7-octenesulfonic acid, poly(perfluoro-3,6-dioxa-4-methyl-7-octenesulfonic acid) and a copolymer of said octenesulfonic acid with tetrafluoroethylene; phosphoric acid; nitric acid; halogenoacids such as perchloric acid, perbromic acid, periodic acid, chloric acid, bromic acid and the like; carboxylic acids such as acetic acid, formic acid, trichloroacetic acid, trifluoroacetic acid, pentafluoropropionic acid, dichloroacetic acid, acrylic acid, poly(acrylic acid) or poly(perfluoro-3,6-dioxa-4-methyl-7-octenic acid, a copolymer of said octenoic acid with tetrafluoroethylene and the like; $HBF_4$, $HPF_6$, $HSbF_4$, $HSbF_6$, $HAsF_6$, $HBCl_3F$ and the like.

Hydrogen halide is excluded from the Brønsted acid according to the present invention. When $X^\ominus$ in N-fluoropyridinium salt used in the method of the present invention is $F^\ominus$ of a conjugate base to hydrogen halide, there is a serious disadvantage in that explosions may break out at above $-2°$ C. because the pyridine $F_2$ complex is unstable. Furthermore, if $X^\ominus$ is $Cl^\ominus$, $Br^\ominus$ and $I^\ominus$, it is difficult to prepare the corresponding N-fluoropyridinium salt.

Amount Of Pyridine Compounds used

In the present invention, it is necessary to use amounts of pyridine compounds greater than an equimolar amount of Brønsted acids.

In the above mentioned Japanese Patent Publication No.2-23707 (column 10, lines 10-13), it is described that "Although an amount of a Brønsted acid compound equimolar to or greater than an amount of a substrate (a pyridine compound: notes by applicant) is used to conduct the reaction with a high yield, an equimolar amount of Brønsted acids is preferably used from an economic view." However, the prior art does not describe at all the technique of the present invention in which an excess amount of pyridine is used. For example, in the above mentioned Japanese Patent Publication No.2-23707 an equimolar amount of pyridine is used relative to an amount of Brønsted acid, and the yield of N-fluoropyridinium salt is as low as 44%.

The present inventors also have found surprisingly that the use of an excess amount of pyridine compound relative to the Brønsted acid dramatically improves the yield almost as much as 100% quantitatively.

As the pyridine compound is used in an amount greater than an equimolar amount of Brønsted acid in the method of the present invention, the amount of pyridine compound is preferably from 1.01 to 1.2 times, more preferably from 1.02 to 1.08 times that of the Brønsted acid.

Fluorine

Fluorine employed in the present invention is preferably used with 99.9% to 50% by volume of an inert gas. Examples of inert gases include nitrogen, helium, argon, tetrafluoromethane, sulfur hexafluoride and the like.

Although the amount of fluorine may be equimolar to or greater than an amount of a pyridine compound, the amount of fluorine required may be appropriately selected when the pyridine compounds are eliminated by reacting with fluorine because the amount of fluorine depends on the introducing methods, reaction temperatures, reaction solvents, reaction apparatus and the like.

A reaction solvent is preferably used in the reaction caused by the method of the present invention. Examples of reaction solvents include acetonitrile, methylene chloride, chloroform, carbon tetrachloride, trichlorofluoromethane, trichlorofluoroethane, ethyl acetate, diethyl ether, tetrahydrofuran and the like or mixture thereof.

A reaction temperature may be selected in the range of $-100°$ C. to $+40°$ C., and a temperature of $-20°$ C. to $0°$ C. leads to preferably a better yield.

EXAMPLES

The method of the present invention may be illustrated with reference to the following examples by using pyridine and 3,5-dichloropyridine as the pyridine compound, and trifluoromethanesulfonic acid and methanesulfonic acid as the Brønsted acid. However, the present invention is not intended to be limited only to the following examples.

EXAMPLE 1

The following reaction was carried out in the present Example.

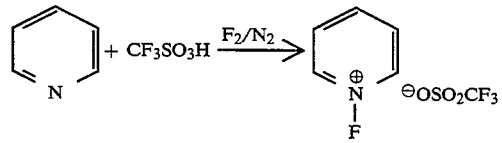

To 40 ml of acetonitrile as solvent were added 1.592 g (20.136 mmol) of pyridine and 2.940 9 (19.588 mmol) of trifluoromethanesulfonic acid (i.e., the amount of pyridine was 1.03 times that of trifluoromethanesulfonic acid in a molar ratio), and the mixture was cooled to $-20°$ C. A mixed gas of fluorine and nitrogen in a volumetric ratio of 1:4 was then introduced to the mixture at a rate of 50 ml/min under stirring. The amount Of fluorine gas introduced was 40.0 mmol. Alter completion of the reaction, the solvent was distilled off, and 4.716 g (19,097 mmol) of N-fluoropyridinium trifluoromethanesulfonate was obtained by crystallizing with ether. The yield was 97.4%. Characteristics and spectrum data of the compound are shown as follows.

Melting point: 175°–178° C.
F-NMR (ppm, $CFCl_3$ internal standard in $CD_3CN$)
$-48.75$ (1F, NF)
77.61 (3F, $CF_3$)
H-NMR (ppm, $CD_3CN$)
9.4 (2H)
8.8 (1H)
8.4 (2H)

EXAMPLES 2–6

The reactions in Examples 2–6 were conducted as in Example 1 except that the molar ratio of pyridine to trifluoromethanesulfonic acid was changed. The results are shown in Table 1.

TABLE 1

| Example | pyridine mmol | $CF_3SO_3H$ mmol | pyridine:$CF_3SO_3H$ (molar ratio) | yield (%) |
|---|---|---|---|---|
| 2 | 19.896 | 19.888 | 1.00:1.00 | 38.8 |
| 3 | 20.224 | 20.617 | 0.981:1.00 | 5.2 |
| 4 | 20.148 | 21.091 | 0.955:1.00 | 2.0 |
| 5 | 20.946 | 19.362 | 1.08:1.00 | 97.5 |

TABLE 1-continued

| Example | pyridine mmol | CF₃SO₃H mmol | pyridine:CF₃SO₃H (molar ratio) | yield (%) |
| --- | --- | --- | --- | --- |
| 6 | 24.271 | 20.230 | 1.20:1.00 | 93.2 |

EXAMPLE 7

The following reaction was carried out in the present Example.

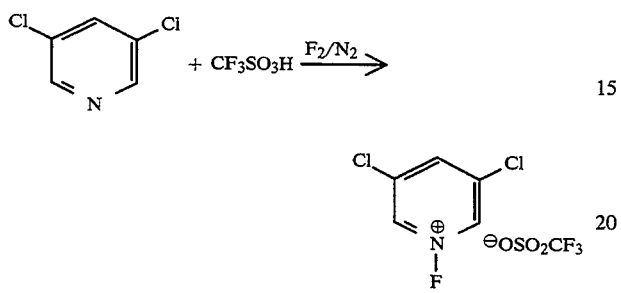

To 40 ml of acetonitrile were added 3.087 g ( 20.860 mmol ) of 3,5-dichloropyridine and 3.039 g ( 20.250 mmol ) of trifluoromethanesulfonic acid ( i.e., the amount pyridine compound was 1.03 times that of trifluoromethanesulfonic acid in a molar ratio), and the mixture was cooled to $-20°$ C. The following procedures were conducted as in Example 1, and 5.774 g (18.3 mmol) of N-fluoro-3, 5-dichloropyridinium trifluoromethanesulfonate were obtained with a yield of 90.0%.

Characteristics and spectrum data of the compound are shown as follows.

Melting point: 116.5°–118° C.
F-NMR ( ppm, CFCl₃ internal standard in CD₃CN )
−52.13 (1F, $J_{H-F}$=14.0 Hz, NF )
77.63 (3F, CF₃ )
H-NMR (ppm, CD₃CN)
9.6 (2H, $J_{H-F}$=14.0 Hz)
8.9 (1H)

EXAMPLE 8

The following reaction was carried out in the present Example.

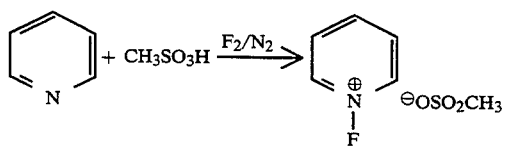

To 40 ml of acetonitrile were added 1.655 g (20.923 mmol) of pyridine and 1,961 g (20.406 mmol) of methanesulfonic acid (i.e., the amount of pyridine was 1,025 times that of methanesulfonic acid in a molar ratio), and the mixture was cooled to $-20°$ C. A mixed gas of fluorine and nitrogen in a volumetric ratio of 1:4 was then introduced to the mixture at a rate of 50 ml/min under stirring. The amount of fluorine gas introduced was 40.0 mmol. After completion of the reaction, the solvent was distilled off, and 3,691 g (19.103 mmol) N-fluoropyridinium methanesulfonate was obtained by crystallizing with ether. The yield was The NMR spectrum data are shown as follows.
F-NMR (ppm, CFCl₃ internal standard in CD₃CN)

−48.75 (NF)

As described above, the method of the present invention leads to a high yield, and does not require filtering out and recrystallization procedures because hydrogen fluoride (HF) produced as a by-product from using Brønsted acids is a compound having a low boiling point (19.5° C). Therefore, the method of the present invention, which can shorten said Japanese Patent's process of preparing N-fluoropyridinium salt, is an epoch-making method for preparing the compound on an industrial scale.

What is claimed is:

1. A method for preparing N-fluoropyridinium salt of the general formula (I):

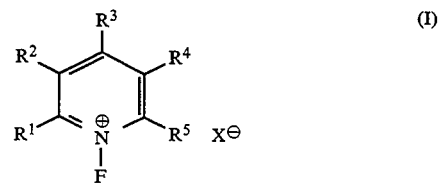

by reacting a pyridine compound of the following general formula (II) with a Brønsted acid of the general formula XH but excluding hydrogen halide and fluorine characterized by using a mole ratio of said formula (II) pyridine compound to said Brønsted acid that is in the range of 1.01 to 1.2:

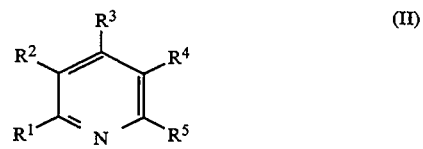

and wherein in each of said general formula (I) and (II) $R^1$ to $R^5$ each represents hydrogen, halogen, alkyl, aryl, acyl, aldoxycarbonyl, aryloxycarbonyl, carbamoyl, nitro, cyano, alkylsulfonyl, arylsulfonyl hydroxy, alkoxy, aryloxy, acyloxy, acylthyio, amido, alkansulfonyloxy or arenesulfonyloxy.

2. The method as claimed in claim 1 wherein said mole ratio is in the range of 1.02 to 1.08.

3. In a method for preparing an N-fluoropyridinium salt by reacting a pyridine compound with fluorine and a Brønsted acid, the improvement which comprises contacting in a reaction solvent at a temperature in the range of $-100°$ C. to $+40°$ C. fluorine with a Brønsted acid of the formula XH but excluding hydrogen halide and a pyridine compound of the general formula:

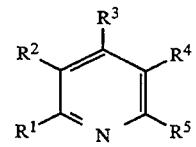

where $R^1$ through $R^5$ are each selected from the group consisting of hydrogen, halogen, alkyl, aryl, acyl, alkoxycarbonyl, aryloxycarbonyl, carbamoyl, nitro, cyano, alkylsulfonyl, arysulfonyl, hydroxy, alkoxy, aryloxy, acyloxy, acylthio, amido alkansulfonyloxy, and arenesulfonyloxy.

4. The method of claim 3 wherein said Brønsted acid contains a sulfonic acid group.

5. The method of claim 3 wherein said mole ratio of said pyridine compound to said Brønsted acid is in the range of 1.02 to 1.08.

6. The method of claim 5 wherein said pyridine compound is selected from the group consisting of pyridine and halo-substituted pyridine, and said Brønsted acid is selected from the group consisting of methanesulfonic acid and halo-substituted methanesulfonic acid.

7. The method of claim 6 wherein said Brønsted acid is selected from the group consisting of methanesulfonic acid and trifluoromethanesulfonic acid.

8. The method of claim 6 wherein said pyridine compound is selected from the group consisting of pyridine and chloro-substituted pyridine.

9. The method of claim 6 wherein said pyridine compound is pyridine, said Brønsted acid is trifluoromethanesulfonic acid, and said N-fluoropyridinium salt is N-fluoropyridinium trifluoromethanesulfonate.

10. The method of claim 6 wherein said pyridine compound is pyridine, siad Brønsted acid is methanesulfonic acid, and said N-fluoropyridinium salt is N-fluoropyridinium methanesulfonate.

11. The method of claim 6 wherein said pyridine compound is a dishloropyridine, said Brønsted acid is trifluoromethanesulfonic acid, and said N-fluoropyridinium salt is an N-fluoro dichloropyridinium trifluoromethanesulfonate.

12. The method of claim 4 wherein said mole ratio of said pyridine compound to said Brønsted acid is in the range of 1.02 to 1.08.

13. The method of claim 12 wherein said pyridine compound is selected from the group consisting of pyridine and halo-substituted pyridine, and said Brønsted acid is selected from the group consisting of methanesulfonic acid and halo-substituted methanesulfonic acid.

14. The method of claim 13 wherein said Brønsted acid is selected from the group consisting of methanesulfonic acid and trifluoromethanesulfonic acid.

15. The method of claim 13 wherein said pyridine compound is selected from the group consisting of pyridine and chloro-substituted pyridine.

16. The method of claim 13 wherein said pyridine compound is pyridine, said Brønsted acid is trifluoromethanesulfonic acid, and said N-fluoropyridinium salt is N-fluoropyridinium trifluoromethanesulfonate.

17. The method of claim 13 wherein said pyridine compound is pyridine, said Brønsted acid is methanesulfonic acid, and said N-fluoropyridinium salt is N-fluoropyridinium methanesulfonate.

18. The method of claim 13 wherein said pyridine compound is a dichloropyridine, said Brønsted acid is trifluoromethanesulfonic acid, and said N-fluoropyridinium salt is an N-fluoro dichloropyridinium trifluoromethanesulfonate.

* * * * *

UNITED STATES PATENT AND TRADEMARK OFFICE
CERTIFICATE OF CORRECTION

PATENT NO. : 5,336,772
DATED : August 9, 1994
INVENTOR(S) : Yukinori Saiki and Kazunori Nukui Page 1 of 3

It is certified that error appears in the above-indentified patent and that said Letters Patent is hereby corrected as shown below:

In the Abstract:

line 3, "Br nsted" should be --Brønsted--;

line 6, "Br nsted" should be --Brønsted--.

Column 1, line 23, "Br nsted" should be --Brønsted--;

Column 1, line 54, "Br nsted" should be --Brønsted--;

Column 2, line 7, "hereto-atom" should be --hetero-atom--;

Column 2, line 9, "hereto-atom" should be --hetero-atom--;

Column 2, lines 67 and 68, "$\Delta^4$-cholestene-3-on-6sulfonic" should be --$\Delta^4$-cholestene-3-on-6-sulfonic--;

Column 3, line 2, "poly(pstyrenesulfonic acid)," should be --poly(p-styrenesulfonic acid),--;

Column 3, line 15, "-octenic" should be --octenoic--;

Column 4, line 34, "2.940 9" should be --2.940 g--;

UNITED STATES PATENT AND TRADEMARK OFFICE
CERTIFICATE OF CORRECTION

PATENT NO. : 5,336,772
DATED : August 9, 1994
INVENTOR(S) : Yukinori Saiki and Kazunori Nukui Page 2 of 3

It is certified that error appears in the above-indentified patent and that said Letters Patent is hereby corrected as shown below:

Column 4, line 40, "amount Of" should be --amount of--;

Column 4, line 41, "Alter" should be --After--;

Column 4, line 43, (19,097 mmol)" should be --(19.097 mmol)--;

Column 5, line 31, "N-fluoro-3, 5-dichloropyridinium" should be --N-fluoro-3,5-dichloropyridinium--;

Column 5, line 56, "1,961" should be --1.961--;

Column 5, line 57, "1,025" should be --1.025--;

Column 5, line 64, "3,691 g(c19.103 mmol)" should be --3.691 g (19.103 mmol) of --;

Column 5, line 66, insert "93.6%." after "was".

Claim 1, column 6, line 38, "formula" should be --formulas--;

UNITED STATES PATENT AND TRADEMARK OFFICE
CERTIFICATE OF CORRECTION

PATENT NO. : 5,336,772
DATED : August 9, 1994
INVENTOR(S) : Yukinori Saiki and Kazunori Nukui It is certified that error appears in the above-indentified patent and that said Letters Patent is hereby corrected as shown below:

Claim 1, column 6, line 40, "aldoxycarbonylonyl" to read --alkoxycarbonyl--.

Claim 3, column 6, line 65, "amido" should be --amido,--;

Claim 5, column 7, line 2, "Br nsted" should be --Brønsted--; and

Claim 10, column 7, line 21, "siad" should be --said--.

Signed and Sealed this

Eighteenth Day of April, 1995

BRUCE LEHMAN

*Commissioner of Patents and Trademarks*

*Attest:*

*Attesting Officer*